(12) United States Patent
Wang (10) Patent No.: US 6,914,674 B1
(45) Date of Patent: Jul. 5, 2005

(54) WEATHER IDENTIFIER FOR SNOW, RAIN, AND DRIZZLE

(75) Inventor: Ting-I Wang, Gaithersburg, MD (US)

(73) Assignee: Optical Scientific, Inc., Gaithersburg, MD (US)

( * ) Notice: Subject to any disclaimer, the term of this patent is extended or adjusted under 35 U.S.C. 154(b) by 181 days.

(21) Appl. No.: 10/372,583

(22) Filed: Feb. 22, 2003

(51) Int. Cl.[7] .............................................. G01N 21/00
(52) U.S. Cl. ..................... 356/338; 250/573; 250/574; 356/73; 356/438
(58) Field of Search ................................ 356/337–343, 356/437, 438, 73, 442; 250/573, 574

(56) References Cited

U.S. PATENT DOCUMENTS

| | | | |
|---|---|---|---|
| 3,745,350 A | * | 7/1973 | Hill et al. ..................... 250/565 |
| 4,693,602 A | * | 9/1987 | Wyatt et al. .................. 356/336 |
| 4,760,272 A | | 7/1988 | Wang |
| 5,373,367 A | * | 12/1994 | DeGunther et al. .......... 356/438 |
| 5,444,530 A | * | 8/1995 | Wang .......................... 356/338 |
| 5,528,224 A | | 6/1996 | Wang |
| 5,604,590 A | * | 2/1997 | Cooper et al. ............... 356/338 |
| 2002/0158215 A1 | * | 10/2002 | Engel et al. ................. 250/573 |

* cited by examiner

*Primary Examiner*—Layla G. Lauchman
(74) *Attorney, Agent, or Firm*—Charles H. Thomas (57) ABSTRACT

A weather identification system is provided which employs a first photosensitive receiver positioned directly in the path of a beam of light a predetermined distance from a partially coherent light beam source. The first photosensitive receiver is in direct optical communication with the light beam source to produce electronic signals in response to scintillations caused by particle movement between the source and the first receiver. A second photosensitive receiver is positioned out of the path of the beam of light and is oriented at an oblique angle relative thereto to provide an output indicative of forward scattering of light from scintillations that occur in the beam of light. The signals from the second photosensitive receiver are AC coupled to provide an output indicative of rate of fluctuation and having a signal strength characteristic that even distinguishes between light drizzle and fog. The weather identification system thereby senses precipitation, categorizes the precipitation as either rain or snow, and drizzle. The weather condition indicating system is ideal for use in remotely monitoring airfields.

4 Claims, 4 Drawing Sheets

WEATHER IDENTIFIER FOR SNOW, RAIN, AND DRIZZLE

BACKGROUND OF THE INVENTION

1. Field of the Invention

The present invention relates to a system for optically and electronically ascertaining the existence and nature of precipitation and for measuring rain, snow, and drizzle in the ambient air from a remote location.

2. Description of the Prior Art

A light emitting diode weather identification system has previously been developed to remotely detect the existence of precipitation and to determine the nature of precipitation. That is, the prior weather identification system can differentiate between rain and snow. This prior weather identification system was established with the intent of automating surface weather observations at airports. The ability to completely automate surface observations is critically dependent on the ability to automatically distinguish between rain and snow. This prior system is disclosed in U.S. Pat. No. 4,760,272 issued on Jul. 26, 1988.

The prior weather identification system is able to correctly identify different types of precipitation in a near field region by transmitting a partially coherent light source over a path length much shorter than that of prior optical precipitation systems. According to the system of U.S. Pat. No. 4,760,272 a partially coherent light source, such as an infrared light emitting diode, may be used in place of a laser source which conventional optical weather identification systems previously required. The partially coherent beam of light is transmitted over a short distance of less then one meter and is detected by an optical receiver located in communication with the transmitter and in spaced separation therefrom.

The percentage light intensity fluctuations (scintillation indices) detected by the optical receiver within certain frequency ranges are indicative both of the existence of precipitation and the nature of the detected precipitation. Frequency components above one kilohertz are indicative of rain. Snow induced frequencies are primarily at a few hundred hertz. Accordingly, electronic signals generated from the received scintillations are directed to at least two different band pass filters to quantify scintillations in low and high frequency ranges. Scintillation signals in the low frequency range indicate snow while scintillations in the higher frequency range indicate rain. The low frequency band may be from twenty five hertz to two hundred fifty hertz, for example, while the high frequency band may extend from one kilohertz to four kilohertz.

Because high frequency components of rain drop induced scintillations are critical for discriminating between rain and snow, a half angle of incoherency which is too large may result in an insufficient number of usable signals in the high frequency band. Therefore, for all practical purposes the product of one half the angle of incoherency of the transmitter, as measured in radians, multiplied by the distance of the transmitter and receiver, must be no greater than about 2.5 millimeters.

While the system of U.S. Pat. No. 4,760,272 quite accurately determines the level of rain and snow, it does not provide an indication of drizzle. As a result of increasingly acute environmental problems, a need existed for accurate sensors to measure drizzle in the atmosphere.

A system was developed to provide a reliable visibility sensor that operates on the principle of forwardscatter in combination with the weather identification system of the type described in U.S. Pat. No. 4,760,272. The visibility sensor of this later development is described in U.S. Pat. No. 5,444,530. The device disclosed in that patent is able to utilize signals from the weather identification portion of the system to neutralize many of the ambiguities that arose in the measurement of light transmission that are unrelated to visibility.

However, it was later learned that even the system of U.S. Pat. No. 5,444,530 had certain shortcomings. Specifically, it is not sensitive enough to detect and identify light drizzle or to distinguish light drizzle from fog. However, according to the present intention, it has been discovered that, with certain modifications, an improved version of that system can be utilized to reliably detect and correctly identify even extremely light drizzle and to distinguish extremely light drizzle from fog.

SUMMARY OF THE INVENTION

It is known that optical forward scattering is sensitive to small particles such as fog and drizzle water droplets. The weather identification and visibility sensor of U.S. Pat. No. 5,444,530 uses the fog-induced forward scattering strength to measure visibility. Although drizzle will also induce forward scattering, a system is required to discriminate between drizzle and fog to reliably detect and identify drizzle.

One major difference between drizzle and fog is that drizzle moves much faster than fog. Therefore, by measuring the fluctuation of the forward scattering, rather than its intensity or strength, the drizzle-induced forward scattering can be separated from that of the fog.

Combining this new system with in-beam optical scintillation, the instrument of the present invention can reliably detect and identify rain, snow, and drizzle. With the addition of an acoustic sensor as described in U.S. Pat. No. 5,528,224, the instrument of the present invention can reliably detect and identify rain, snow, drizzle, ice pellets, and hail. U.S. Pat. No. 5,528,224 is hereby incorporated by reference in its entirety.

In one broad aspect the present invention represents an improvement to a weather identification system having a light beam source that transmits a partially coherent beam of light along a prescribed path, a first receiver positioned directly in the light beam path to produce signals in response to scintillations occurring in the beam of light, and signal processing means for producing a signal from the first receiver characteristic of rain and another signal from the first receiver characteristic of snow. Also, a second receiver is obliquely positioned relative to the prescribed path to produce output signals responsive to forward scattering of light from scintillations occurring in the beam of light. The signal processing means is responsive to output signals from both the first and the second receivers to produce a signal characteristic of visibility in the ambient air through which the light beam travels.

According to the improvement of the present invention the signal processor means employed is modified from that of U.S. Pat. No. 5,444,530 so as to measure the fluctuation of the signal indicative of forward scattering of light from the second receiver, rather than the intensity of light from the second receiver. This produces an output from the signal processor that is characteristic of rain, including extremely light drizzle, and which does not mistake fog for drizzle.

In the present invention a single light source is shared by both the first receiver, which is employed to detect and identify precipitation, and the second or offbeam receiver which is employed to provide an indication of drizzle. The light intensity detected by the second or offbeam receiver is normalized by the intensity detected by the first receiver or inbeam detector to obtain the forward scattering coefficient which is independent of the light source intensity. This system is therefore immune from fluctuation of the source intensity and from dust on the optical system. In addition, because the fluctuation rather than strength of forward scattering from the second detector is measured, the signal output reliably indicates fine drizzle, but not fog.

In another broad aspect the invention may be considered to be a weather condition indicating system comprising: a partially coherent light beam generating transmitter arranged to transmit a partially coherent beam of light along a linear path, a frequency modulating circuit for driving the partially coherent light beam generating transmitter with a carrier frequency; a first photosensitive receiver positioned directly in the path of the beam of light at a predetermined distance therefrom and in direct optical communication therewith; a first preamplifier circuit coupled to amplify signals from the first receiver generated in response to scintillations occurring in the light beam from the transmitter; a second photosensitive receiver positioned out of the path of the beam of light and at an acute angle relative thereto, a second preamplifier circuit coupled to amplify signals from the second receiver generated in response to forward scattering of weather particles in the beam; and a signal processor. The signal processor separably isolates signals from the first receiver having frequency characteristics of rain and of snow and from the second receiver having a fluctuation in strength characteristic of drizzle.

The improved weather identification system of the invention has several major optical electrical component assemblies. These are: an infrared transmitting module, a transmitter optical assembly, a receiver optical assembly, an automatic gain control normalizer, a signal processor, and a microprocessor unit.

One major concern of the system design is to ensure that the signal received by the receiver optical assembly maintains a high enough signal to noise ratio under various types of background light contamination. Such contamination is inevitably present to varying degrees due to sunshine, street lights and other sources. The infrared emitting diode is driven by a modulator to ensure that the system is immune to the background noise.

The infrared light emitted from the infrared emitting diode is collected by the transmitter optics to form a partially coherent light beam. This partially coherent light beam is pointed to the receiver optics which is located about 0.4 meters away. Particles falling through the beam will modulate the beam to induce light scintillation of the received signal. The receiver optical assembly employs a horizontal line aperture so as to be sensitive to the vertical motion of the precipitation.

The modulated light is detected by a first PIN photodiode followed by a first preamplifier and an automatic gain controlled (AGC) receiver. The AGC receiver acts as a normalizer to overcome the problems associated with power fluctuations caused by temperature change, component aging, dust on the lens and weather obscuring effects such as those produced by fog and haze. The output of the AGC receiver is demodulated and directed to the signal processor. Within the signal processor two major frequency bands of the scintillation spectrum are selected. Specifically, a high frequency band pass filter is employed to isolate signals in the one kilohertz to four kilohertz range, and a low frequency band pass filter is employed to isolate signals in the twenty five to two hundred fifty hertz range. The outputs of the high band pass filter and low band pass filter are used for quantitative rain and snow intensity measurements and an identification of the precipitation state. The signal of the high bandpass filter is proportional to the rain intensity, and the signal from the low bandpass filter is proportional to the snow intensity. The ratio of the high bandpass filter signal to the low bandpass filter signal is used to discriminate rain from snow.

To further increase the sensitivity of detecting a precipitation event, a particle counting channel is also used. The signal processor also provides a channel to monitor the carrier signal strength and to detect accidental blocking of the light beam or light source failure.

In the weather identification system of the invention a second receiver is positioned out of the path of the beam of partially coherent light and at an acute angle of alignment relative thereto. The second receiver has an optical section designed to collect the maximum amount of scattered light induced by precipitation. A second preamplification circuit is coupled to the second receiver to amplify the signals therefrom. These signals are then directed through a narrow band pass filter to reject the background noise.

The carrier signal as detected by the first receiver is then shifted in phase to match the output of the second receiver. The filtered signal from the second, off axis receiver, together with the phase shifted received carrier from the first receiver, are then fed into a synchronous detection stage to measure the fluctuation in signal strength with a predetermined time constant of ten milliseconds or less. The integrated output of the synchronous detection stage is then AC coupled to a root mean square converter to produce a logarithmic output of signals from the second photosensitive receiver. This is done to increase the dynamic range of the signal level.

The invention may be described with greater clarity and particularity by reference to the accompanying drawings.

DESCRIPTION OF THE EMBODIMENT

Figure 1:
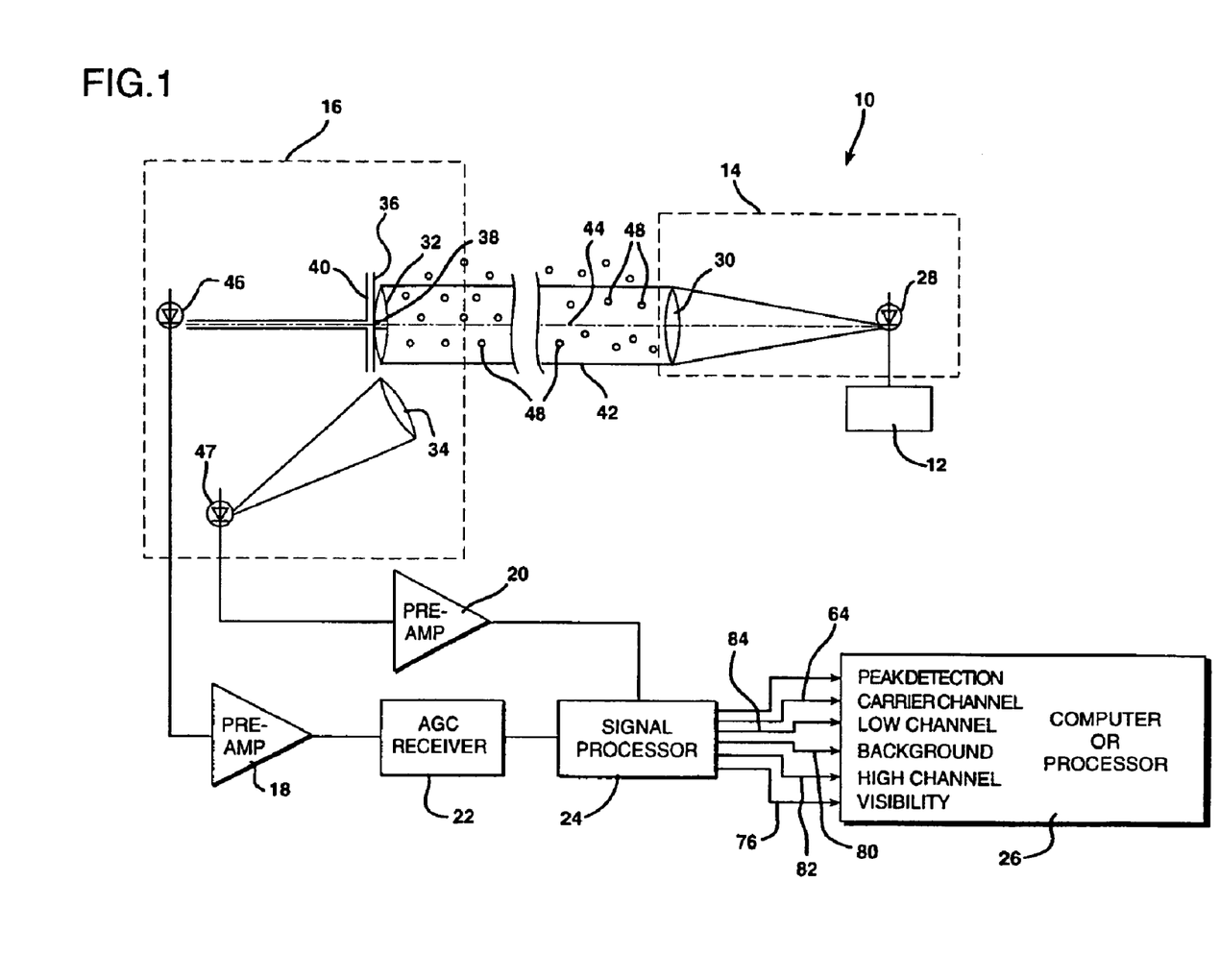
FIG. 1 is a functional block diagram of a preferred embodiment of the weather condition indicating system according to the invention.

The present invention is based upon and operates much in the manner of the weather identification and visibility sensing system of U.S. Pat. No. 5,444,530, which is incorporated herein in its entirety by reference. FIG. 1 is a functional block diagram illustrating a weather identification system generally at 10 constructed according to the present invention. The weather identification system 10 includes an infrared (IRED) transmit modulator 12, a transmitter optical assembly 14, a receiver optical assembly 16, preamplification circuits 18 and 20, an AGC receiver 22, a signal processor 24, and a microprocessor unit 26.

The transmitter optical assembly employs an infrared light emitting diode 28 and a one hundred millimeter transmitter culminating lens 30. The carrier signal generator 12 is coupled to produce a carrier signal at about forty six kilohertz to drive the light beam transmitting IRED photo transmitting diode 28.

The receiver optical assembly 16 includes a first photosensitive receiver lens 32 having a focal length of one hundred millimeters and a second receiver lens with a focal length of 75 millimeters 34. The first receiver lens 32 employs a mask 36 which defines a horizontal slot 38 one millimeter in height and which is located directly behind the first receiver lens 32. An infrared filter 40 is located behind the mask 36.

The transmitter 14 produces a partially coherent light beam 42. The first photosensitive receiver lens 32 is located a predetermined distance, preferably 0.4 meters, from the transmitter optical assembly 14 that serves as the partially coherent light beam source. The first photosensitive receiver lens 32 is focused on a PIN photodiode 46. The PIN photodiode 46 produces electronic signals in response to scintillations caused by the movement of particles, indicated collectively at 48, that move between the light beam source 14 and the first photosensitive receiver lens 32. The electronic signals is then amplified by the preamplifier 18.

Figure 2:
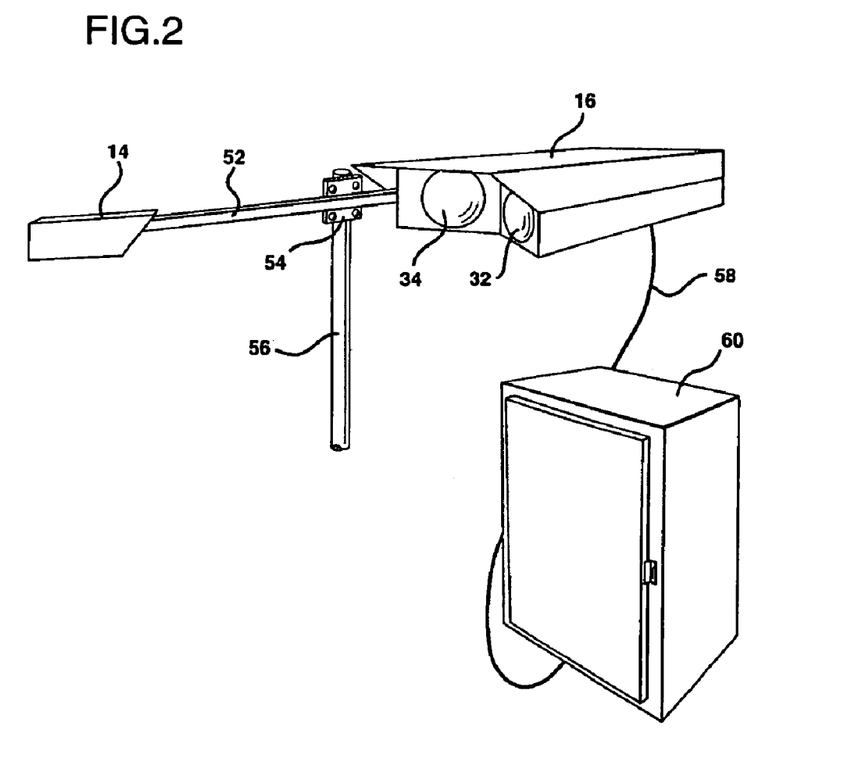
FIG. 2 is a perspective view illustrating the physical mounting and configuration of the optical components and the housing for the electronic components of the system of FIG. 1.
Figure 3:
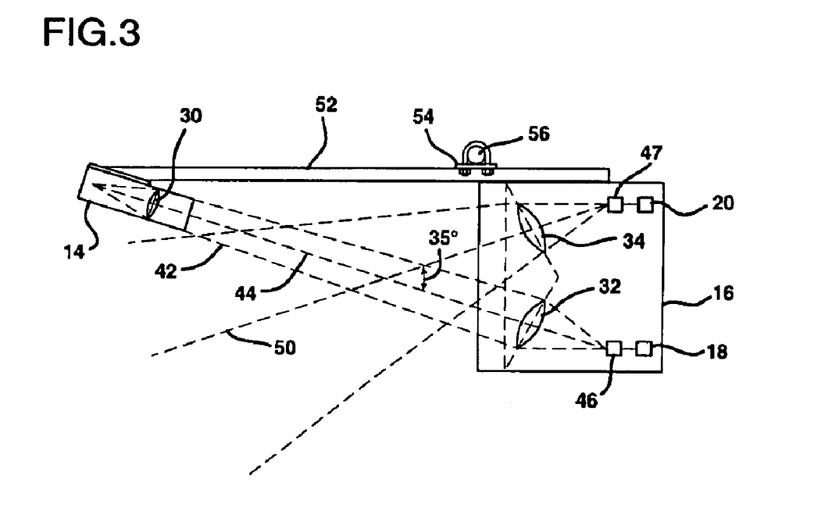
FIG. 3 is a diagrammatic top plan view illustrating the geometry of the optical components of FIG. 2.

As illustrated in FIGS. 2 and 3, the second photosensitive receiver lens 34 is located off axis or out of the path 44 of the light beam 42 obliquely and at an acute angle relative thereto. The second photosensitive receiver lens 34 is focused on a second PIN photodiode 47 that is identical to the photodiode 46. This signal of the PIN photodiode 47 is amplified by the preamplifier 20.

As shown in FIG. 3, the transmitter lens 30 is aligned to transmit the partially coherent beam of light 42 centered along a linear path indicated at 44. The center of the first photosensitive receiver lens 32 is aligned directly in the path 44 and in direct optical communication with the light beam 42 which focuses light on the PIN photodiode 46 that in turn produces electronic signals in response to scintillations caused by movement of the precipitation particles 48.

The second, offbeam photosensitive receiver lens 34 is aligned at an oblique, acute angle relative to the light beam path 44. The axis of alignment of the second lens 34 is indicated at 50 in FIG. 3. The linear axis 50 is oriented to intersect the path 44 of the light beam at an angle that may vary between about twenty five degrees and forty five degrees. Preferably, the axis of alignment 50 of the second photosensitive receiver lens 34 intersects the light beam path 44 at an acute angle of about thirty five degrees.

The physical configuration and arrangement of the optical components is illustrated in FIG. 2. The transmitter optical assembly 14 is laterally encased within a sensor head that is mounted on a horizontal beam 52 that is secured by a mounting bracket 54 to a vertical support mast 56. The receiver optical assembly 16 is likewise laterally enclosed. The first and second photosensitive receiver lenses 32 and 34, respectively, are level with each other and the receiver mask 36 is horizontal.

The transmitter optical assembly 14 and the receiver optical assembly 16 should be installed about six feet above the surrounding terrain, and the support mast 56 should be firmly embedded in the ground and should not sway or vibrate excessively in the wind. The mast 56 can be easily mounted on a tower or a cement platform. The receiver optical assembly 16 should be installed so that the axis of alignment 50 of the offbeam receiver lens 34 is preferably directed northward in the northern hemisphere so as to avoid any possible interference from the sun. The installation of other optical instruments nearby should be planned so that such instruments do not point directly at the receiver optical assembly 16.

Electrical signals and power are transmitted through conductors within a cable 58 to a weathertight electronic housing cabinet 60 that contains the transmit modulator 12, the AGC receiver 22, the signal processor 24 and the microprocessor 26. The electronics cabinet 60 also includes power supplies and lightning protection devices. The casing 60 is a NEMA-4 rated weather proof enclosure.

The infrared transmitter modulator 12, the transmitter optical assembly 14, the first photosensitive receiver lens 32, the mask 36, the infrared filter 40, the PIN diode 46, the first preamplifier 18, the AGC receiver 22, and the portion of the signal processor 24 which processes signals from the AGC receiver 22 are fully described in U.S. Pat. No. 4,760,272, the disclosure of which is also incorporated herein in its entirety by reference. The novelty of the invention resides in the combination of a forward scattering drizzle sensor that analyses the fluctuation in intensity of light received from the second receiver. Because drizzle moves much faster than fog, a higher rate of fluctuation is indicative of drizzle, while a lower rate of fluctuation is characteristic of fog.

Figure 4:
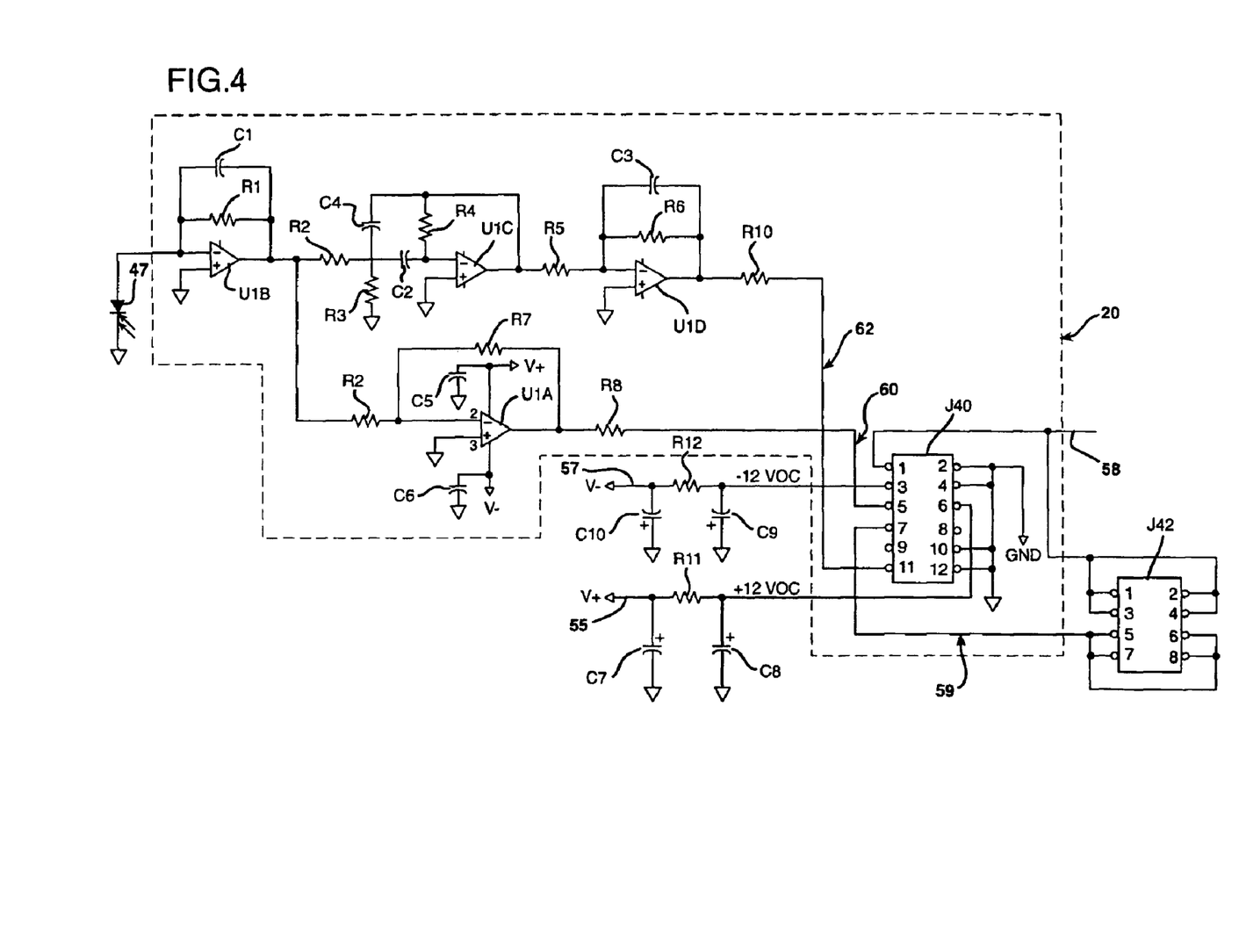
FIG. 4 is a schematic diagram illustrating the electronic components of the photosensitive receiver and preamplifier circuit employed to generate and amplify signals used to determine visibility.
Figure 5:
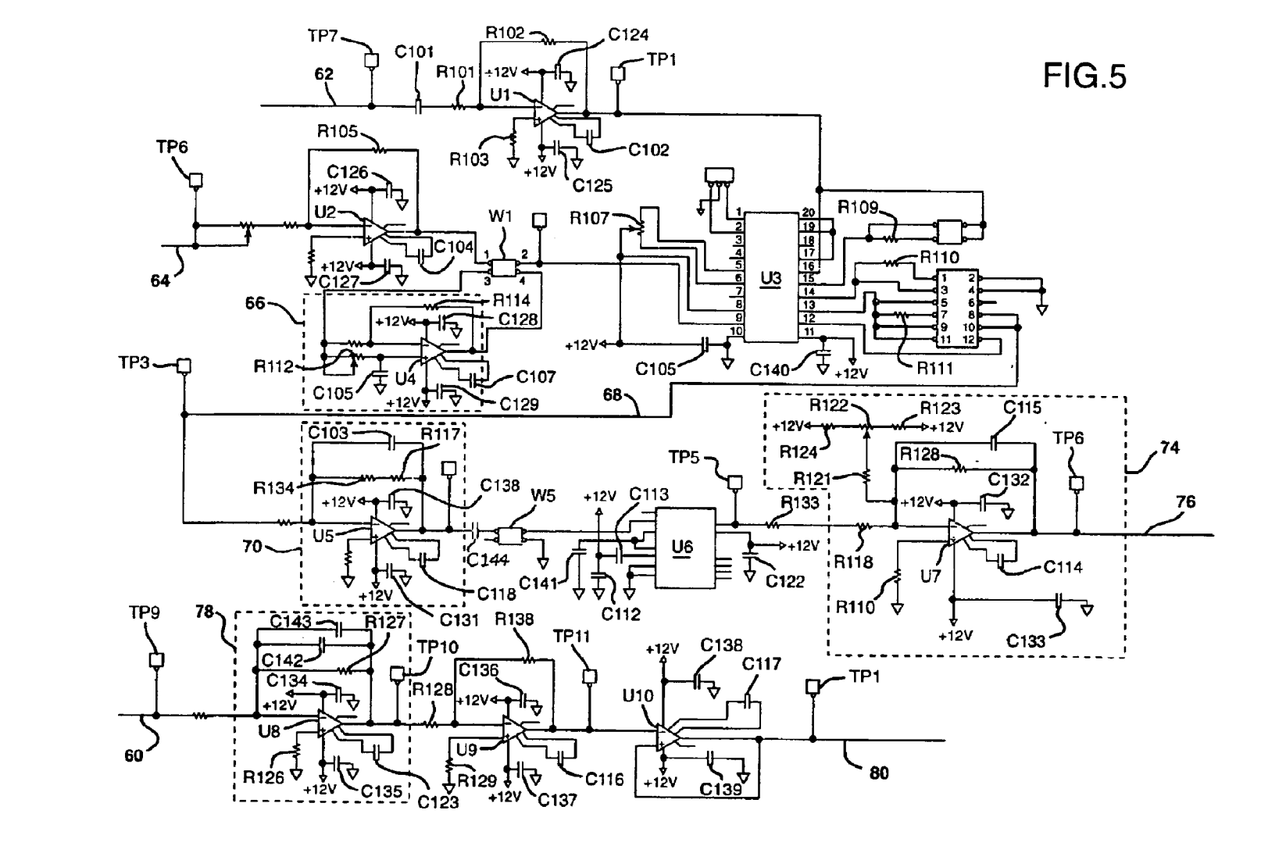
FIG. 5 is a schematic diagram illustrating the portion of the signal processor for isolating and processing signals from the photosensitive receiver of FIG. 4 to produce signals having a strength characteristic of visibility.

The electronic components utilized for the derivation of the output of the second off axis photosensitive receiver lens 34 are illustrated schematically in FIGS. 4 and 5. The suggested resistor and capacitor values for the circuit of FIG. 4 are set forth in Table 1 while those of FIG. 5 are set forth in Table 2. All of the amplifiers U1A, U1B, U1C and U1D in FIG. 4 are LF347N operational amplifiers, while all of the amplifiers U1, U2, U4, U5, U7, U8, U9 and U10 are LM101 operational amplifiers.

The PIN offbeam receiver photodiode 47 shown schematically in FIG. 4 is identical to the PIN inbeam receiver photodiode 46, both of which may be Litronix BPX61 PIN photodiodes, each of which has an active area of 2.7 millimeters square. The output of the photodetector 47 is directed to operational amplifier U1B which is the operative component of a current to voltage converter circuit that includes the capacitor C1 and resistor R1. The voltage signal from the output of amplifier U1B is passed as an input to amplifier U1C in a bandpass filter circuit. This band pass filter is centered at forty six kilohertz, which is the frequency of the carrier signal produced by the frequency modulating circuit or carrier signal generator 12, depicted in FIG. 1. The signal from the band pass filtering amplifier U1C is passed through resistor R5 as an input to a gain stage amplifier circuit employing an amplifier U1D. The output of amplifier U1D is directed as an input to pin 11 of a junction block J40.

The signal from the current to voltage converter amplifier U1B is also directed to an input of amplifier U1A in a direct current coupling circuit. This circuit measures the background light as detected by the photosensitive receiver lens 34. The output of amplifier U1A is indicative of the magnitude of background light and is transmitted as a input to pin 5 of junction block J40.

The preamplifier circuit 20 is supplied with a positive twelve volt direct current power signal on line 55 and a negative twelve volt direct current signal on line 57. These power signals are filtered through resistor-capacitor networks as illustrated in FIG. 4 and appear as power inputs at pins 6 and 3 of the junction block J40, as shown.

The lens 34, like the lens 32, has a lens heater that is employed to evaporate moisture that might otherwise condense on it. To keep the transmitter and receiver lenses free of dew and frost, PTC thermistor heaters are bonded to the insides of these lenses. A thermistor is placed on each lens well below the central horizontal aperture area. The thermistors are continuously turned on during the operation of the weather condition indicating system. Power to the lens heater for the lens 34 is delivered through a lens heating junction block J42. The lens heating system operates on the fifteen volt direct current differential of power supplied on lines J8 and J9. This lens heating system is conventional and is described in U.S. Pat. No. 4,760.272, and is therefore not illustrated in FIG. 4.

The inputs from amplifiers U1A and U1D are respectively supplied to input pins 5 and 11 in junction block J40. The preamplified output signal from amplifier U1A appears on line 60, while that of amplifier U1D appears on line 62.

The signals on lines 60 and 62 from the preamplifier circuit 20 are then coupled to the signal processor 24. As previously noted, the signal processor 24 includes circuitry for processing the signals from the inbeam photosensitive receiver diode 46 as described in U.S. Pat. No. 4,760,272, and that portion of the circuitry is not repeated herein, but is incorporated by reference. However, the signal processor 24 also includes circuitry for processing the signals from the offbeam receiving photodiode 47. Specifically, the gain amplified signal on line 62 is connected to test point TP7, shown in FIG. 5, while the background light intensity signal on line 60 is connected to test point TP9 in FIG. 5. In addition, the signal processor 24 receives a signal from the AGC receiver 22 on line 64 at test point TP6 in FIG. 5.

The signal on line 62 from the second preamplifier circuit 20 is passed through amplifier U1 in a gain stage circuit. The amplified output from amplifier U1 is provided as an input to a demodulating circuit U3 at pin 17 thereof. Demodulated circuit U3 is an AD636 demodulation unit.

The signal 64 from the AGC receiver 22 is connected to a gain stage amplifier circuit as an input to amplifier U2. The output of the gain stage amplification circuit is connected as an input to pin 1 of connection block W1, the output at pin 3 of which is carried to amplifier U4 in a phase shifting circuit 66. The purpose of phase shifting circuit 66 is to synchronize the phases of signals from the first and second preamplifier circuits 18 and 20, which are respectively coupled to the first and second photosensitive receiver photodiodes 46 and 47. The phase shifting circuit 66 includes a resistor pot R112 which must be adjusted to match the phase of the signal on line 64 with the phase of the signal on line 62. The phase shifting circuit 66 adjusts the phase of the signal from the AGC receiver 22 on line 64 to synchronize the phase of that signal with the signal on line 62 from the preamplifier circuit 20. The output of the phase shifting 66 is coupled as an input at pin 4 and an output of pin 2 of the connecting strip W1 and coupled as an input on pin 5 to the demodulating circuit U3.

The demodulating circuit U3 demodulates the synchronized signals at pins 5 and 17 to remove the carrier frequency therefrom. The demodulator circuit U3 multiplies the signal at pin 5 from the first preamplifier circuit 18 and the signal at pin 17 from the preamplifier circuit 62 to produce a synchronized direct current output signal which is the product of those two inputs. This output signal appears on line 68 and is proportional to the ratio of the intensity of light received from the second photosensitive receiver lens 34 to that received from the first photosensitive receiver lens 32. The demodulator U3 ignores all signal components in the signals received on pins 5 and 17 except those components that are exactly in phase and at the same frequency, which is the carrier frequency of 46 kilohertz. The direct current output on line 68 is essentially a fully rectified sine wave where it appears at test point TP3. The demodulator output on line 68 is then directed as an input to amplifier U5 in an integration circuit indicated generally at 70.

The critical differences between the integration circuit 70 of the present application and the corresponding circuit described in prior U.S. Pat. No. 5,444,530 is that the signal input to amplifier U6 is converted from DC coupling to AC coupling detection. Specifically, the large capacitor previously coupled across the input and output of amplifier U5 is removed and the value of capacitor C103 is reduced from one to 0.022 microfarads. Also, a two hundred twenty microfarad capacitor C144 is positioned at the last stage of integration circuit 70 in circuit between the output of amplifier U5 and connecting block W5. The time constant formed by C144 and the input impedance of U6 should be about ten seconds or less. With these changes from the system of U.S. Pat. No. 5,444,530, the output 76 measures the fluctuations of the forward scattering that is dominated by drizzle, rain, and snow. Fog-induced forward scattering usually changes slower than ten seconds. It will not be a major contributor to the fluctuations of the forward scattering. Therefore, the output 76 can reliably detect drizzle, rain, and snow, but not fog.

The integrated output from the integration circuit 70 is directed through a connecting block W5 to a root mean square to direct current conversion circuit U6. The output of conversion circuit U6 is directed to amplifier U7 in a buffer amplifier circuit indicated generally at 74. The buffer amplifier circuit 74 has a resistor pot R122 which is used to shift the signal for calibration purposes. The output signal from the buffer amplifier circuit 74 appears at TP5 and as an output on line 76 to the microprocessor 26.

The output signal on line 76 has a strength characteristic of visibility, as derived from the second photosensitive receiver lens 34. The signal on line 76 has a magnitude proportional to the logrithm of the extinction coefficient. That is, it is proportional to the logrithrn of the scattered light intensity fluctuations. By providing the signal as a logrithrn, the dynamic range of the drizzle sensor is greatly expanded.

The signal processor 24 also produces a background intensity signal from the input received from the preamplifier circuit 20 on line 60. The signal on line 60 appears at test point TP9 and is directed to an amplifier U8 in an integration circuit 78. The integration circuit 78, unlike the integration circuit 70, produces a direct current output signal at test point TP10 with respect to the same time constant of the integration circuit 70, which is ten seconds.

The integrated output from integration circuit 78 at test point TP10 is directed as an input to amplifier U9 of a gain amplification circuit, the output of which appears at test point TP11. The gain amplified signal from test point TP11 is directed as an input to an amplifier U10 of a buffer amplifier circuit, the output of which appears at test point TP12 and as an output on line 80 to the microprocessor 26. The output on line 80 is proportional to background light intensity. The signal on line 80 is employed to differentiate daytime and nighttime measurements.

The microprocessor 26 is formed of a single board containing an Intel MCS51 family controller, a 16 channel, 12 bit analog to digital converter section, memory, firmware, and a serial I/O section (RS-232C). The microprocessor 26 contains software for self testing, diagnostic analysis, a weather algorithm, and communications which allow the weather condition indicating system 10 to be used for remotely monitoring a site of interest.

The weather condition indicating system 10 constructed according to the invention is extremely reliable. False alarms of reports of precipitation when no precipitation exists occur at a rate of less than 0.2 percent, while a false identification rate in distinguishing rain from snow and drizzle from fog with some form of precipitation is less than one percent. The error in intensities of precipitation is less than five percent for precipitation of levels from 0.4 inches per hour to four inches per hour, and less than ten percent at precipitation levels of from 0.004 inch per hour to twenty inches per hour.

Undoubtedly, numerous variations and modifications of the invention will become readily apparent to those familiar with conventional optical weather identification and measurement systems. Accordingly, the scope of the invention should not be construed as limited to this specific embodiment thereof depicted and described herein.

TABLE 1

| | | |
|---|---|---|
| R1 | 221 | K ohms |
| R2 | 9.53 | K ohms |
| R3 | 1 | K ohms |
| R4 | 95.3 | K ohms |
| R5 | 4.02 | K ohms |
| R6 | 34.7 | K ohms |
| R7 | 10 | K ohms |
| R8 | 1.0 | K ohms |
| R9 | 10 | K ohms |
| R10 | 1.0 | K ohms |
| R11 | 2.7 | ohms |
| R12 | 2.7 | ohms |
| C1 | 5 | picofarads |
| C2 | 330 | picofarads |
| C3 | 47 | picofarads |
| C4 | 330 | picofarads |
| C5 | 0.1 | microfarads |
| C6 | 0.1 | microfarads |
| C7 | 100 | microfarads |
| C8 | 100 | microfarads |
| C9 | 100 | microfarads |
| C10 | 100 | microfarads |

TABLE 2

| | | |
|---|---|---|
| R101 | 2.0 | K ohms |
| R102 | 100 | K ohms |
| R103 | 0 | ohms |
| R104 | 5.0 | K ohms |
| R105 | 5.0 | K ohms |
| R106 | 5.0 | K ohms |
| R107 | 1.0 | K ohms |
| R109 | 5 | K ohms |
| R110 | 10 | K ohms |
| R111 | 10 | K ohms |
| R112 | 5.0 | K ohms |
| R113 | 5.0 | K ohms |
| R114 | 5.0 | K ohms |
| R115 | 100 | K ohms |
| R116 | 0 | ohms |
| R117 | 8 | K ohms |
| R118 | 6.5 | K ohms |
| R119 | 0 | ohms |
| R120 | 150 | K ohms |
| R121 | 221 | K ohms |

TABLE 2-continued

| | | |
|---|---|---|
| R122 | 50 | K ohms |
| R123 | 95.0 | K ohms |
| R124 | 75.0 | K ohms |
| R125 | 221 | K ohms |
| R126 | 0 | ohms |
| R127 | 221 | K ohms |
| R128 | 10 | K ohms |
| R129 | 0 | ohms |
| R130 | 10 | K ohms |
| R131 | 2.2 | ohms, 2W |
| R132 | 2.2 | ohms, 2W |
| R133 | 150 | ohms |
| R134 | 221 | K ohms |
| C101 | 0.01 | microfarads |
| C102 | 15 | picofarads |
| C103 | 0.022 | microfarads |
| C104 | 15 | picofarads |
| C105 | 0.1 | microfarads |
| C107 | 15 | picofarads |
| C108 | 0.041 | microfarads |
| C110 | 150 | picofarads |
| C112 | 0.1 | microfarads |
| C113 | 10 | microfarads |
| C114 | 100 | picofarads |
| C115 | 1.0 | microfarads |
| C117 | 100 | picofarads |
| C118 | 100 | microfarads |
| C119 | 100 | microfarads |
| C120 | 100 | microfarads |
| C121 | 100 | microfarads |
| C122 | 0.1 | microfarads |
| C123 | 150 | picofarads |
| C124 | 0.1 | microfarads |
| C125 | 0.1 | microfarads |
| C126 | 0.1 | microfarads |
| C127 | 0.1 | microfarads |
| C128 | 0.1 | microfarads |
| C129 | 0.1 | microfarads |
| C130 | 0.1 | microfarads |
| C131 | 0.1 | microfarads |
| C132 | 0.1 | microfarads |
| C133 | 0.1 | microfarads |
| C134 | 0.1 | microfarads |
| C135 | 0.1 | microfarads |
| C137 | 0.1 | microfarads |
| C138 | 0.1 | microfarads |
| C139 | 0.1 | microfarads |
| C140 | 0.1 | microfarads |
| C142 | 1 | microfarads |
| C143 | 47 | microfarads |
| C144 | 220 | microfarads |

I claim:

1. In a weather identification system having a light beam source that transmits a partially coherent beam of light along a prescribed path, a first receiver positioned directly in said light beam path to produce signals in response to scintillations occurring in said beam of light, a second receiver obliquely positioned relative to said prescribed path to produce output signals responsive to forward scattering of light from scintillations occurring in said beam of light and a signal processing means, wherein said signal processing means has means for detecting a signal indicative of intensity of light received from said light beam by said first detector, means for detecting a signal indicative of light intensity of said forward scattering of light from said second receiver, and means for synchronizing said signal indicative of light intensity of said forward scattering of light and said signal indicative of intensity of light from said light beam to produce said signal characteristic of drizzle, said signal processing means being responsive to output signals from both said first and second receivers to produce a signal from said first receiver characteristic of rain and another signal from said first receiver characteristic of snow that is independent of intensity of said light source, the improvement wherein said signal processing means also measures the fluctuation of said signal indicative of forward scattering of light from said second receiver so that said signal characteristic of rain is characteristic of rain that includes drizzle and excludes fog.

2. In a weather identification system having a light beam source that transmits a partially coherent beam of light along a prescribed path, a first receiver positioned directly in said light beam path to produce signals in response to scintillations occurring in said beam of light, signal processing means for producing a signal from said first receiver characteristic of rain and another signal from said first receiver characteristic of snow, a carrier signal generator coupled to produce a carrier signal to drive said light beam source, a second receiver obliquely positioned relative to said prescribed path to produce output signals responsive to forward scattering of light from scintillations occurring in said beam of light and wherein said signal processing means is responsive to output signals from both said first and said second receivers to produce a signal characteristic of precipitation, the improvement comprising: synchronizing means coupled to receive said output signals from said second receiver and said carrier signal from said first receiver to produce a synchronized output in the form of a demodulated direct current signal proportional to fluctuation of the level of forward scattering occurring in said beam of light, integrating means for integrating said synchronized output with a predetermined time constant, and a root mean square to current converter circuit for producing said signal characteristic of precipitation as a signal proportional to the logarithm of intensity of forward scattered light.

3. A weather condition indicating system comprising:
a partially coherent light beam generating transmitter arranged to transmit a partially coherent beam of light along a linear path,
a frequency modulating circuit for driving said partially coherent light beam generating transmitter with a carrier frequency,
a first photosensitive receiver positioned directly in said path of said beam of light at a predetermined distance therefrom and in direct optical communication therewith,
a first preamplifier circuit coupled to amplify signals from said first receiver generated in response to scintillations occurring in said light beam from said transmitter,
a second photosensitive receiver positioned out of the path of said beam of light and oriented at an acute angle relative thereto,
a second preamplifier circuit coupled to amplify signals from said second receiver generated in response to forward scattering of scintillations, and
a signal processor for separately isolating signals from said first receiver having frequency characteristics of rain and of snow and from said second receiver having a strength characteristic of drizzle, and including a phase shifting circuit for synchronizing the phases of signals from said first and second preamplifier circuits, and a demodulating circuit coupled to said phase shifting circuit to demodulate synchronized signals from both said first and second preamplifier circuits to produce a synchronized direct current output signal proportional to the product of the fluctuation in intensity of light received from said second receiver to the intensity of light received from said first receiver in order to produce said signal from said second receiver having a strength characteristic of visibility.

4. A weather identification system comprising:
a partially coherent light beam source, arranged to transmit a beam of light along a linear path,
a carrier signal generator coupled to drive said light beam source with a carrier signal,
a first photosensitive receiver positioned directly in said path of said beam of light a predetermined distance from said partially coherent light beam source and in direct optical communication therewith to produce electronic signals in response to scintillations caused by particle movement between said source and said first receiver,
a first preamplification circuit coupled to said first photosensitive receiver to produce an output indicative of said carrier signal input to said first photosensitive receiver,
a second photosensitive receiver positioned out of said path of said beam of light and oriented at an acute angle relative thereto to provide an output indicative of forward scattering of light from scintillations in said beam of light,
a second preamplification circuit coupled to said second photosensitive receiver,
a signal processing means coupled to both said first and second preamplification circuits for producing first, second and third outputs for detected scintillations wherein said first output has a frequency range above about one kilohertz characteristic of rain, said second output has a frequency range lower than that of said first output and characteristic of snow, and said third output has a signal strength characteristic of drizzle and wherein said signal processing means is comprised of a phase shifting circuit coupled to said first preamplification circuit for adjusting the phase of said carrier signal input to said first photosensitive receiver to match the phase of said output from said second photosensitive receiver, a demodulation circuit coupled to said phase shifting circuit and to said second preamplifier circuit to produce an alternating current signal indicative of fluctuation in said output from said second photosensitive receiver synchronized with said carrier signal output from said first preamplification circuit, and a root mean square to current converter coupled to said demodulation means to produce said signal characteristic of drizzle as a direct current voltage directly proportional to the logarithm of intensity of forward scattering of scintillations detected by said second receiver.

* * * * *